United States Patent [19]

Barker, Jr. et al.

[11] Patent Number: 5,628,756

[45] Date of Patent: May 13, 1997

[54] KNOTTED CABLE ATTACHMENT APPARATUS FORMED OF BRAIDED POLYMERIC FIBERS

[75] Inventors: Boyd T. Barker, Jr., Memphis; Eric Lange, Cordova, both of Tenn.

[73] Assignee: Smith & Nephew Richards Inc., Memphis, Tenn.

[21] Appl. No.: 681,697

[22] Filed: Jul. 29, 1996

Related U.S. Application Data

[63] Continuation of Ser. No. 346,852, Nov. 30, 1994, Pat. No. 5,540,703, which is a continuation-in-part of Ser. No. 100,458, Jul. 30, 1993, Pat. No. 5,456,722, which is a continuation of Ser. No. 1,065, Jan. 6, 1993, abandoned.

[51] Int. Cl.⁶ .................................................. A61B 17/10
[52] U.S. Cl. ........................... 606/139; 606/224; 606/228
[58] Field of Search ................................ 623/13, 17, 228, 623/1, 66; 606/224, 228, 139

[56] References Cited

U.S. PATENT DOCUMENTS

| | | | |
|---|---|---|---|
| 5,234,435 | 8/1993 | Seagrave | 623/13 |
| 5,306,301 | 4/1994 | Graf et al. | 623/13 |
| 5,397,356 | 3/1995 | Goble et al. | 623/13 |

*Primary Examiner*—Michael Buiz
*Assistant Examiner*—Kevin Truong
*Attorney, Agent, or Firm*—Pravel, Hewitt, Kimball & Krieger

[57] ABSTRACT

A surgical, orthopaedic cable attachment apparatus and method for the surgical repair or fusion of orthopaedic anatomical structures is constructed from a length of flexible cable formed of a braided polymeric material having a first and second end portion. A first loop is formed in the first end portion of the cable with a second loop is formed, being placed around or through the bone parts to be tied. After the second loop is place around the selected bone parts, the free cable end is passed through the first loop and pulled tight to define a tightened position. The free cable end can have a needle. The free end is then secured to the cable by splicing for example, to hold the cable in the tightened position.

22 Claims, 13 Drawing Sheets

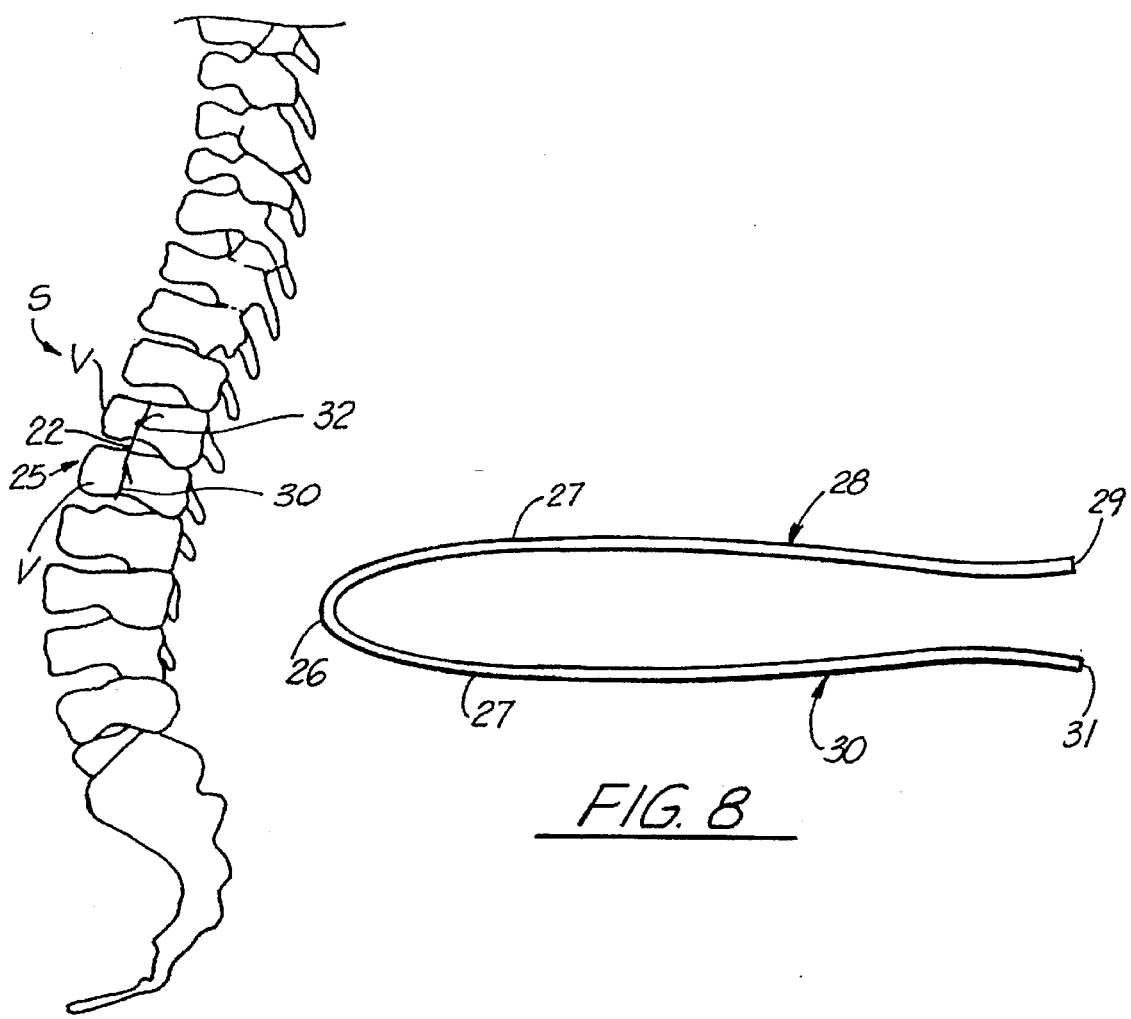
FIG. 7
FIG. 8
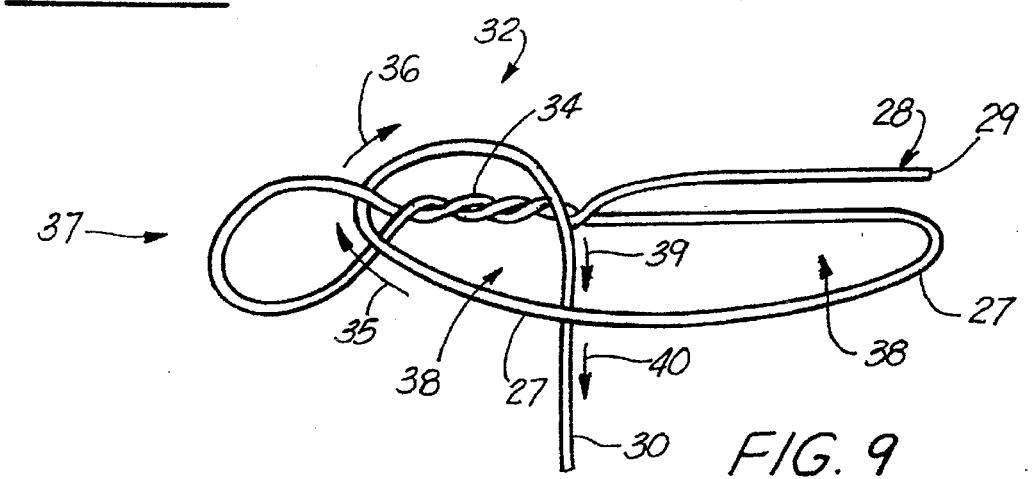
FIG. 9

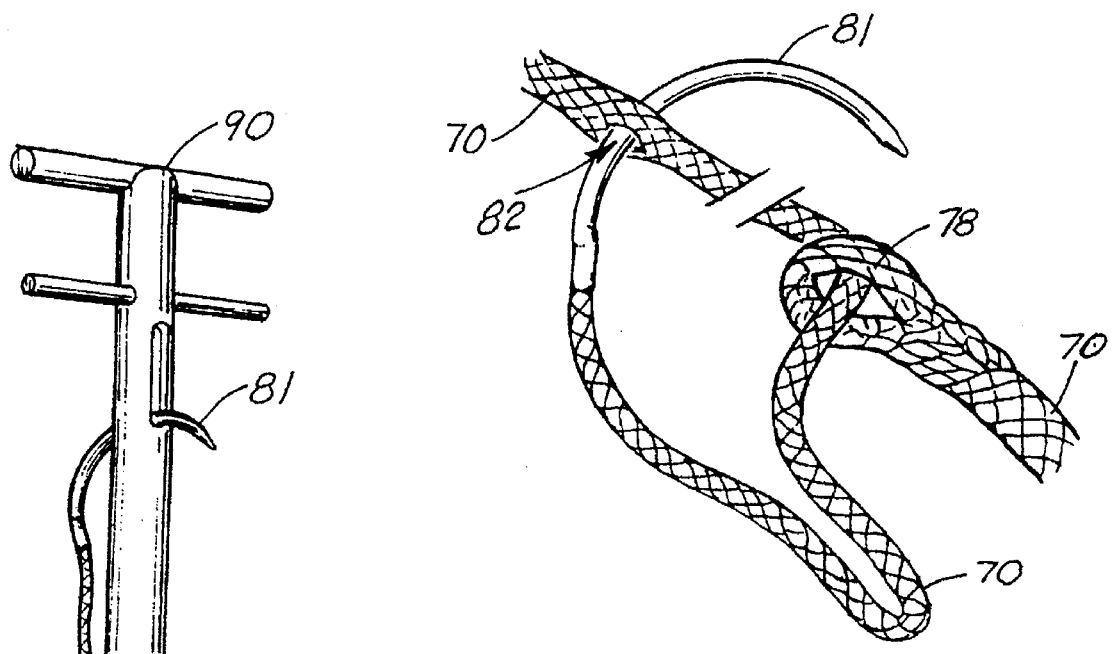
FIG. 30
FIG. 32
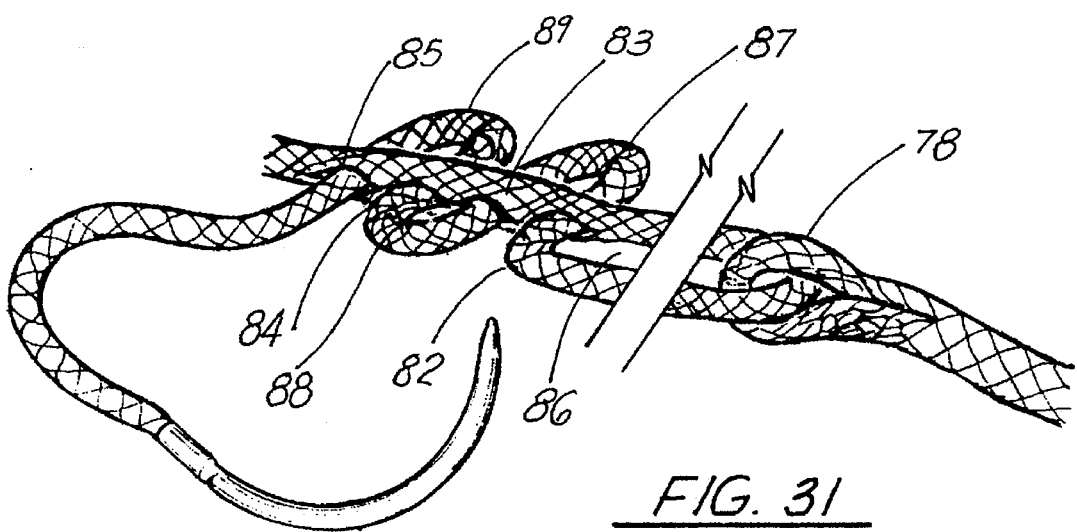
FIG. 31

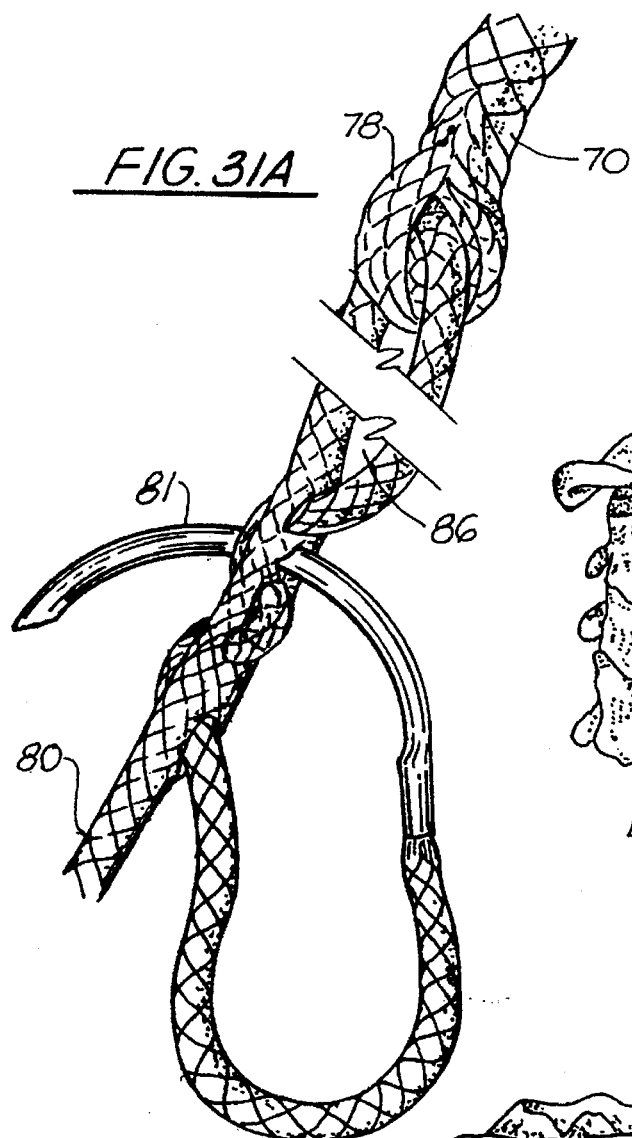
FIG. 31A
FIG. 38
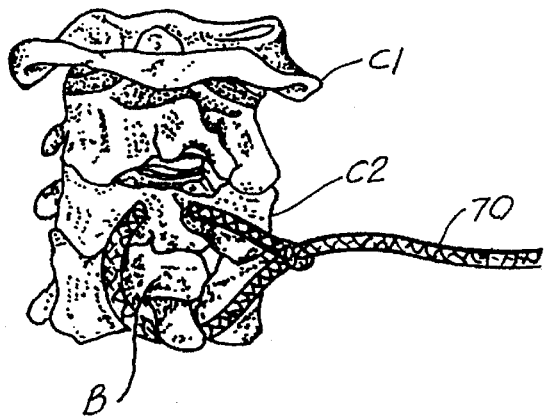
FIG. 37
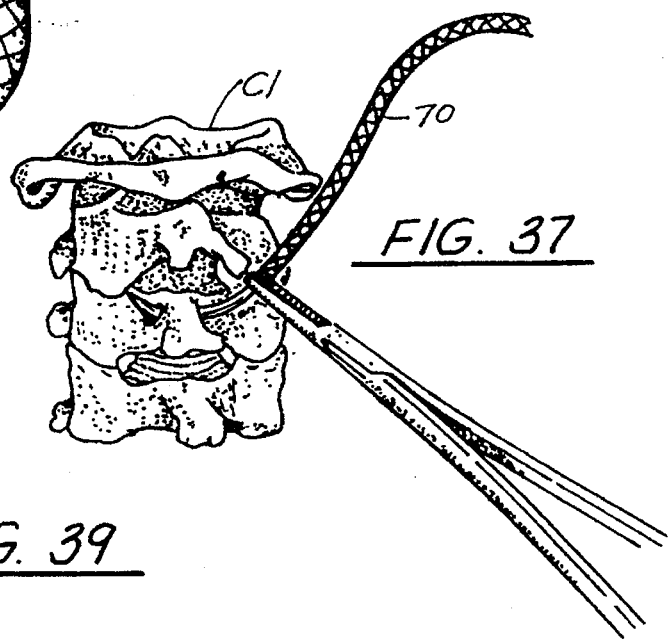
FIG. 39
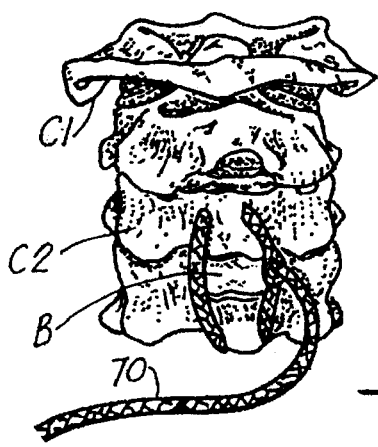

KNOTTED CABLE ATTACHMENT APPARATUS FORMED OF BRAIDED POLYMERIC FIBERS

This is a continuation of application Ser. No. 08/346,852, filed Nov. 30, 1994, now U.S. Pat. No. 5,540,703, which is a continuation-in-part of Ser. No. 08/100,458, filed Jul. 30, 1993, now U.S. Pat. No. 5,456,722, which is a continuation of Ser. No. 08/001,065, filed Jan. 6, 1993, now abandoned.

BACKGROUND OF THE INVENTION

1. Field of the Invention

The present invention relates to a surgical cable attachment apparatus and more specifically to a non-loosening, tensionable, knotted surgical cable attachment apparatus formed of braided polymeric material and a surgical method of the fracture fixation, bone fusion and ligament reattachment.

2. General Background

Surgical procedures for the repair or fusion of large and small bones, ligaments and tendons, and other orthopedic procedures frequently require use of an orthotic device or attachment apparatus which can be subject to tensioning and bear heavy loads caused by the unique anatomical features of the compromised bone or tendon. For example, fractures of the patella are exposed to high stresses during flexion and extension of the knee joint; fusions of the spinal vertebrae are exposed to high gravitational forces and movements of the spinal column; torn ligaments and tendons are exposed to high stresses due to contraction of the associated muscle or flexion and extension of the bony structures; and trochanteric reattachment and cerclage techniques involve cable that is tensioned and exposed to high weight loads and stress factors.

An orthotic or attachment device used in such a fashion must be able to bear heavy stress loads, be flexible enough to achieve the desired repair, and be sufficiently inelastic to maintain alignment of the anatomical structures for proper fusion and repair.

SUMMARY OF THE INVENTION

Materials currently available for such surgical procedures include synthetic or wire sutures, metal cable and various specialized prosthetic or orthotic devices. Synthetic and metal sutures are susceptible to fatigue and breakage during application and use. The currently available synthetic suture materials have insufficient strength and stiffness to provide the stress sharing and strain-limiting capabilities required. Metal cable or wire sutures, while providing additional strength, lack the flexibility required for many fusion and/or repair procedures, and are succeptable to breakage due to fatigue.

Satisfactory repair or fusion requires that the bones or bone fragments remain sufficiently immobilized to permit healing. Current procedures for the repair or fusion of small bones including vertebrae and the patella, restrict motion of the bones or bone fragments by wiring the elements into the appropriate position. The applied surgical wire is generally bent tightly around the bone fragments and two ends of the wire are generally twisted together to provide compressive force.

Breakage of wire sutures or cables may occur with bending during implantation of the device or post-implantation movement generating repetitive bending stresses. Failure of the wire to supply sufficient compressive force and apposition of bone fragments results in reduced or failed healing of the bones. Sharp wire points caused by wire breakage in situ can result in significant damage to surrounding tissues and/or joint capsules.

Metal suture material is radiopaque, and interferes with efficient X-ray monitoring of bone fusion and repair. Metal sutures also interfere with the use of magnetic resonance imaging diagnostic procedures which require that no metal be present in the vicinity of use.

It would be highly desirable to provide a small diameter, flexible, load bearing suture to replace low strength polymeric or synthetic sutures and metal sutures for use in the fusion, repair, and augmentation of small bones, ligaments, and tendons.

A material has been developed that has the unique properties of high tensile and fatigue strength, low stretch, high abrasion and cut resistance, and a high surface lubricity. This material is formed of a high strength, biocompatible, organic polymer, preferably polyolefins, such as high strength polypropylene or ultra high molecular weight polyethylene which can be braided into a cable.

It has been found that a braided cable formed of strong polymeric fibers produces a load bearing suture of sufficient tensile strength, flexibility and stiffness to be useful in the repair and fusion of small bones, ligaments and tendons.

The polymeric braided cable of the present invention has strength at least equivalent to that of a metal suture, and much greater flexibility. The present invention does not exhibit the problems associated with metal fatigue and breakage of wire, and may be formed with a much smaller diameter.

The polymeric braided cable of the present invention may also be formed of a bioresorbable polymer, eliminating the necessity of removing the cable and allowing gradual transfer of stress to the tissue or bone over time.

The load bearing cable of the present invention has the following characteristics: greater tensile strength than available polymeric suture materials; greater stiffness than available suture materials; greater flexibility and fatigue lifetime than metal sutures; transparent to x-rays and does not interfere with magnetic resonance imaging; tightly woven to discourage tissue ingrowth.

The load bearing cable of the present invention is formed of a plurality of high tensile strength polymeric fibers, each of which is less than 100 microns in diameter and has a tensile strength of greater than or equal to about 350,000 psi, and preferably greater than 500,000 psi. To form the load-bearing cable, a plurality of such fibers are formed into a hollow braid having a longitudinal bore extending through the center. The load bearing cable may be formed from as few as one ply or as many as six ply bundles of approximately 120 individual fibers per ply. Preferred is a two-ply, eight strand braided cable preferably less than 3 mm in diameter and most preferred is a one ply, eight strand braided cable less than 1 mm in diameter.

It has been found that a cable attachment apparatus formed of these fibers offers great potential in many orthopedic and non-orthopedic applications as well as non-medical applications. However, the material's surface lubricity makes it difficult to tie a fast tensionable knot in the cable. Presently used knotting techniques for the cable include back-to-back granny knots, however, these knots present a problem as the knots slip or break before less than 50% of the cable's strength is tensioned. Although this failure strength might be adequate given the anatomical loads of the body, surgeons need to be able to tension as well as hold fast the attachment apparatus in order to provide an adequate union between tendons and ligaments, bone fragments and other bony structures in need of repair or fusion.

Therefore, it would be highly desirable to provide a knotted cable attachment apparatus constructed from a braided polymeric material formed of ultra high molecular weight polyethylene.

The invention is directed to a cable attachment apparatus for the surgical repair or fusion of bones, ligaments and tendons, and other bony structures which can be subject to tensioning and heavy bearing loads. The invention is also directed to a method of forming the cable attachment apparatus with preferably non-loosening tensionable knots. The cable attachment apparatus can be used in both medical and non-medical applications.

In one embodiment the cable attachment apparatus is constructed from a length of flexible cable having first and second ends, by forming a first non-self-loosening knot in a first portion of the cable to create a relatively large adjustable loop. The first end is pulled to tighten the first knot with the second cable end being accessible to adjust the size of the loop. The first end of the cable is then tied to the loop through a second non-self-loosening knot to create an opening in a second portion of the cable which is placed around an object to be tied. The second cable end is pulled to reduce the size of the loop and tighten the opening around the object to be tied.

The flexible cable is formed of a braided polymeric material formed of high strength, biocompatible, organic polymer, preferably polyolefins such as ultra-high molecular weight polyethylene.

BRIEF DESCRIPTION OF THE DRAWINGS

A better understanding of the invention can be obtained when the detailed description of exemplary embodiments set forth below is reviewed in conjunction with the accompanying drawings, in which:

FIG. 7 is a side plan view of a human spinal column with a cable attachment apparatus of the present invention securing adjacent vertebrae together;

FIGS. 8–9 are top plan views of the formation of the first non-self-loosening knot of the present invention;

FIGS. 30–32 are schematic sequential views that illustrate a splicing method for use with the method of the present invention;

FIGS. 37–39 are schematic sequential views illustrating the method of the present invention.

DETAILED DESCRIPTION OF THE PREFERRED EMBODIMENT

FIGS. 1 through 6 illustrate the exemplary embodiments of a load bearing cable 10 of the present invention. Although the cable of the present invention is shown as connecting specific small bones and/or ligaments, the cable can also be used in the repair of other small bones and soft tissues.

Figure 5:
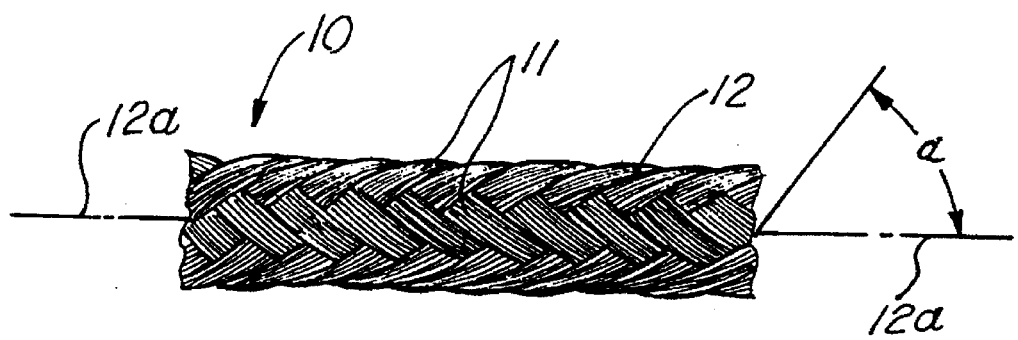
FIG. 5 is a longitudinal view of a braided load bearing cable of the present invention.

As shown in FIG. 5, the load bearing, braided cable 10 is formed of a plurality of biocompatible polymeric fibers wound as bundles of parallel fibers into yarns 11. Yarns 11 of from one to six ply are then wound into strands 12. The strands 12 are then intertwined to form the braided cable 10, for example, an eight-strand diamond braid. In a preferred embodiment, the polymeric fibers are bundled into yarns of approximately 650 denier, the yarns are wound into 1 to 6 ply, and more preferably one or two-ply strands, and the strands are braided into a single, hollow, plain 8-strand diamond braid. The braided construction allows utilization of high strength fibers as individual units while providing negligible bending resistance. Preferably, the resulting braid contains approximately 9 to 13 ticks per inch.

In rope terminology, a plain braid is defined according to the number of picks per inch. A "pick" is defined as a crossing of one yarn bundle over another, with the number of picks counted across the longitudinal axis. The greater number of picks per inch, the tighter the braid. In the preferred embodiment, a braid having approximately 9 to 13 picks per inch provides a flexible cable having a desired diameter of less than 3 mm.

The fibers are formed of a high strength, biocompatible, organic polymer, preferably polyolefins such as high strength polypropylene or ultra-high molecular weight polyethylene. U.S. Pat. No. 4,413,110, to Kavesh et. al, which is hereby incorporated by reference, describes one process for the production of ultra-high molecular weight polyethylene (UHMWPE) fibers which have a high tenacity and a high tensile modulus. Any suitable means for providing UHMWPE will suffice.

Commercial embodiments of the polyethylene fibers described in the Kavesh patent are known by the trademarks SPECTRA-900 and SPECTRA-1000 and are sold by Allied-Signal, Inc. These commercially available fibers have a tensile strength of about 375,000–425,000 psi per individual monofilament. The density of each monofilament is between 0.5 and 1.5 g/cc, preferably about 0.97. Fibers of SPECTRA-1000 have a tenacity of approximately 35 g/denier, a specific gravity of 0.97 and an average diameter of 27 microns (0.0011 inch). Each monofilament is less than 100 microns in diameter. Fibers are assembled to form a tight weave which discourages fibrous ingrowth. Preferably, pore sizes are less than 30 microns. For UHMWPE, the cable 10 is optimally formed of 8 strands, each strand having from one to six ply. Each single ply strand contains approximately 120 fibers of UHMWPE. Thus, the preferred embodiment of the braided load-bearing cable 10 has from 960 individual fibers for a one ply braid to 1920 individual fibers for a two ply braid.

Preferably the load bearing cables of the present invention have a diameter of approximately less than three millimeters and can carry loads of up to 550 pounds. For example, a single ply 8-strand diamond braid can withstand a load of approximately 180 lbs. and a double ply can withstand a load of approximately 320 lbs.

The cables of the present invention are formed with the strongest available biocompatible polymer and optionally with a biocompatible resorbable polymer. The upper limit imposed on the strength of the polymer is the flexibility required.

In one embodiment, the polymeric fibers of the present invention are bioresorbable. Suitable fibers are, for example, those formed of polylactic acid or polyglycolic acid.

Examples of materials useful in the present invention are ultra-high molecular weight polyethylene fibers, each having a tensile strength of at least 350,000 psi. Especially preferred is the ultra-high molecular weight polyethylene, e.g., Spectra-1000. The surface of the fibers may be modified, for example toughened, for ease of fixation of the cable.

Figure 6:
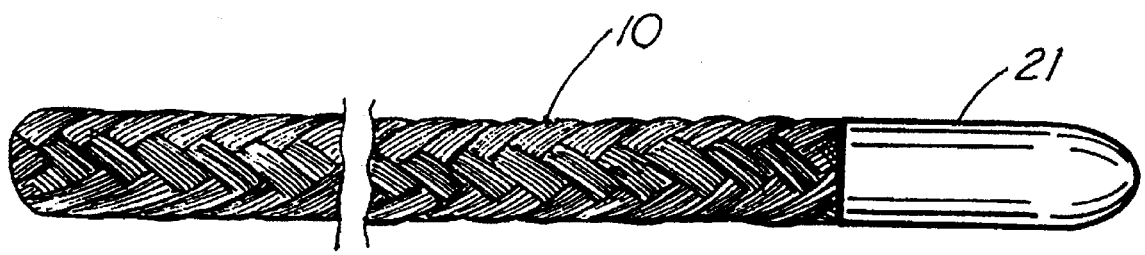
FIG. 6 is a pictorial view of a load bearing cable of the present invention swaged to a needle.

The load bearing cable of the present invention may be utilized in a variety of surgical procedures to fuse or repair small bones and ligaments and tendons. For example, the cable may be used as an orthosis and shield the torn ligament or tendon from the normal stress and strain until the tissue has healed, e.g. by sewing the cable through remnants of a ligament and bringing the torn ends into opposition. To facilitate such use, the cable 10 may be attached to a needle 21 as shown in FIG. 6, or similar device for threading the cable 10 through tissues.

Alternatively, the cable may be used to shield normal stress and strain until the tissue has become strong enough to carry the full amount of stress, e.g. by sewing the cable through a replacement tissue graft. The load bearing cable of the present invention may also be substituted for surgical wire or cable in the repair of small bone fractures such as the patella or bone fusions such as vertebral fusions. The cable has sufficient tensile strength to maintain bone fragments in close approximation to promote active healing and is sufficiently inelastic to prevent separation of fragments under tensile loading. The load bearing cable is less susceptible to fatigue failure than surgical wire. In the event the cable does fail, no threat of damage to surrounding tissue is posed.

Characteristics of the structure of the present invention and its application may be better understood by reference to the examples which follow:

EXAMPLE 1

Fatigue Testing of Metal Surgical Sutures

Titanium orthopedic cable having a diameter of 0.045 inch and cobalt chromium orthopedic cable having a diameter of 0.045 inch were tested for bending fatigue. The titanium cable was Ti-6Al-4V (ASTM F-136) and the cobalt chrome was ASTM F-90. A 15 inch length of the metal cable was installed on a bending fixture for fatigue testing. A loading rod was fixed to a load cell and the fatigue test fixture was positioned so that the loading rod was directly above the cable. Operating in stroke control the loading rod was moved downward against the cable until a load of two pounds was read. The displacement of the crosshead at this two pound load was recorded. The rod was then advanced until a load of 20 pounds was indicated, and this displacement was recorded. Still in stroke control, a sinusoidal function varying between the two previously recorded displacements was established at a rate of 0.5 Hz. This created a load variation on from 2 to 20 pounds on the cable, with resultant bending around the rod. Testing continued until the cable broke. This testing was performed on six titanium cables and six cobalt chromium cables. The results are shown in Table 1.

TABLE 1

| CABLE MATERIAL | AVG CYCLES TO FAILURE |
| --- | --- |
| COBALT CHROMIUM | 18,408 (S.D. 4854) |
| TITANIUM | 8,042 (S.D. 1161) |

EXAMPLE 2

Fatigue Testing of a Cobalt-Chrome Surgical Cable

Testing was performed on a cobalt-chrome surgical cable ASTM F-562 (Richards MP35N), 0.044 inches in diameter in a bending fixture as described for Example 1. The pulley system was cycled at a rate of 0.7 Hz at displacements that resulted in the plunger seeing an axial load that varied between 2 to 20 pounds. Cycling was halted upon failure. The average fatigue life was 56,700 cycles.

EXAMPLE 3

Fatigue Testing of Braided UHMWPE Surgical Cable

An ultra-high molecular weight polyethylene braided cable was fabricated from Spectra 1000™ fiber. Yarns of approximately 650 denier were arranged as single ply and two-ply strands, and braided into an 8-strand hollow diamond braid.

The braided cable was fatigue tested in a bending fixture as described in Example 1. The springs had a spring constant of 6 lbs/in. The pulley radius was one inch. The distance between pulley centers was three inches. The load plunger had a radius of 0.2 inches. Each test was conducted at 1 Hz.

During fatigue testing, the surgical cable or metal suture was subjected to a sinusoidal plunger load of from 2-20 pounds-force (lbf). The springs provided resistance to the plunger load. The material was also subjected to a pre-load of approximately 7.5 lbf due to the tensioning of the springs.

The polymeric ultra high molecular weight polyethylene cable of the present invention was attached to the springs by tying a knot in both ends of the braid and searing the knot with heat. The knot was then passed through a ring and set screw and a set screw was tightened down to secure the braid to the spring.

Because the cable was flexible, the loading was considered a purely tensile load. Therefore, a static analysis was used to determine the tension in the cable. A single ply braid having a cross-sectional diameter of approximately 0.040 inches (1 mm) and a two-ply braid having a cross-sectional diameter of approximately 0.060 inches (1.52 mm) were tested. The maximum stress in each cable was 401 psi for the single ply and 267 psi for the two ply cables.

Before testing, half of the ultra high molecular weight polyethylene braids were treated to roughen the surface of the braid for enhancement of knot holding capability of the braid by application of a charged plasma to the surface of the braid.

Five tests were run for each of the single ply and two ply braids in both treated and untreated conditions. The results are shown in Table 2. The single ply and two ply braided ultra high molecular weight polyethylene surgical cable in both treated and untreated conditions survived 100,000 cycles in the bending fixture described above. There were no braid failures or knot failures in any of the tests taken to 100,000 cycles.

Fatigue testing of metal surgical cables using the same procedure and protocol indicated that MP35N cables (cobalt-chrome) had a fatigue life of 56,700 cycles as discussed in Example 2. Testing of titanium and Co-Cr surgical cable using the same protocol and procedures determined the fatigue life to be 8,042 cycles and 18,408 cycles, respectively, as discussed in Example 1. These results indicate the braided polymeric cable of the present invention has a better fatigue life than the metal cables formed of cobalt-chrome, or titanium. The charged plasma surface roughening treatment did not effect the fatigue life of the braid.

TABLE 2

FATIGUE STRENGTH OF UHMWPE BRAIDED CABLE

| PLY | ROUGHENING TREATMENT | CYCLES |
| --- | --- | --- |
| SINGLE | UNTREATED | 100,000 |
| SINGLE | UNTREATED | 100,000 |
| SINGLE | UNTREATED | 100,000 |
| SINGLE | UNTREATED | 100,000 |
| SINGLE | UNTREATED | 100,000 |
| SINGLE | TREATED | 100,000 |
| SINGLE | TREATED | 100,000 |
| SINGLE | TREATED | 100,000 |
| SINGLE | TREATED | 100,000 |
| SINGLE | TREATED | 100,000 |
| TWO-PLY | UNTREATED | 100,000 |
| TWO-PLY | UNTREATED | 100,000 |
| TWO-PLY | UNTREATED | 100,000 |
| TWO-PLY | UNTREATED | 100,000 |
| TWO-PLY | UNTREATED | 100,000 |
| TWO-PLY | TREATED | 100,000 |
| TWO-PLY | TREATED | 100,000 |
| TWO-PLY | TREATED | 100,000 |
| TWO-PLY | TREATED | 100,000 |
| TWO-PLY | TREATED | 100,000 |

EXAMPLE 4

Repair of Anterior Cruciate Ligament

The anterior CRUCIATE ligament of the knee connects the femur to the tibia, preventing the tibia from sliding anteriorly beneath the femur. As shown, for example in FIG. 3, to repair or reconstruct a torn anterior cruciate ligament, the load bearing cable 10 of the present invention is anchored to both the femur 13 and the tibia 14. Anchorage to bone may be via surgical staple, pins, or screws 15. The cable 10 is sewn along the axis of the normal ligament, and thus bears all or part of the tensile load normally borne by the native ligament. The cable replaces a cast, cast-brace or brace normally required to immobilize the joint after surgery and permits healing of the tissue graft by acting as an internal splint to shield the tissue from stress while permitting some joint motion during the post-operative period. This procedure alleviates loss of tensile strength in the tissue graft normally associated with Joint immobilization following surgery. Once satisfactory tissue strength is achieved in the graft, the cable may be removed.

When a bioresorbable cable is used to augment the ligament, the cable will resorb over a suitable time for healing, gradually transferring load to the tissue graft.

EXAMPLE 5

Repair of Patella Fracture

Figure 1:
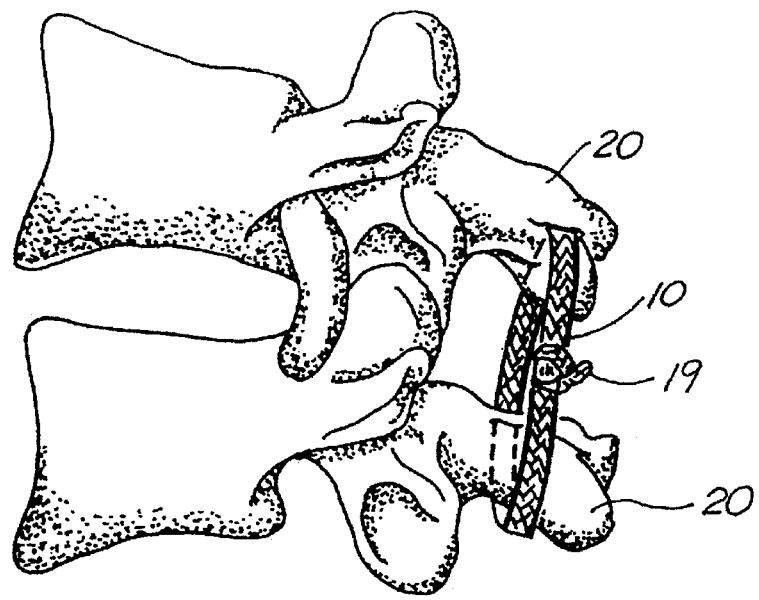
FIG. 1 is a pictorial view of the load bearing cable of the present invention as applied to adjacent vertebrae in a spinal column fusion.
Figure 2:
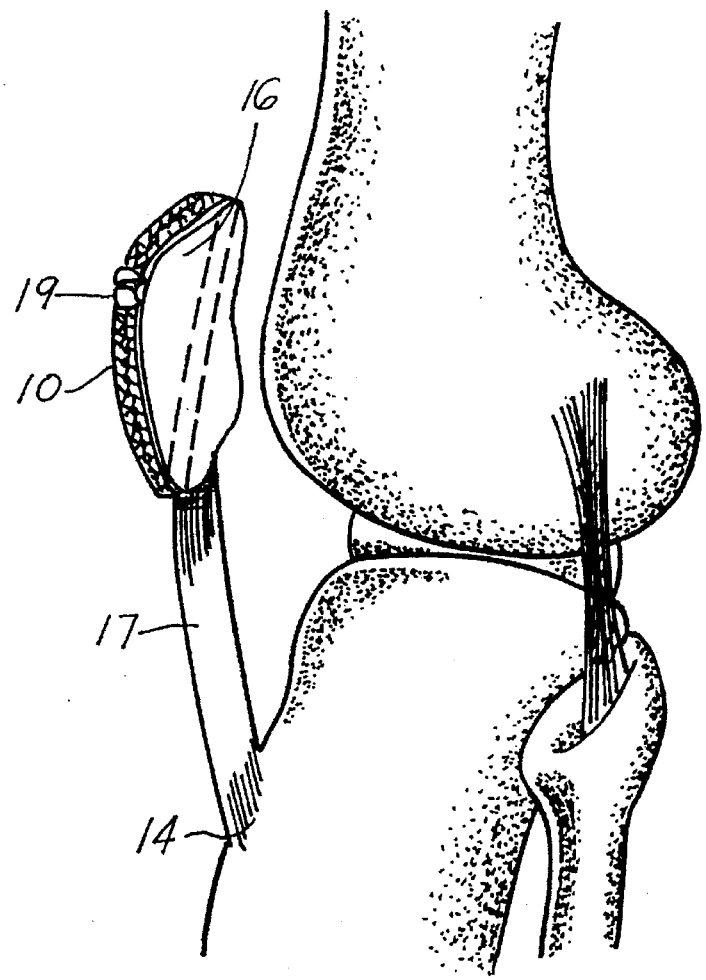
FIG. 2 is a pictorial view of the load bearing cable of the present invention as applied to repair of a fractured patella.
Figure 3:
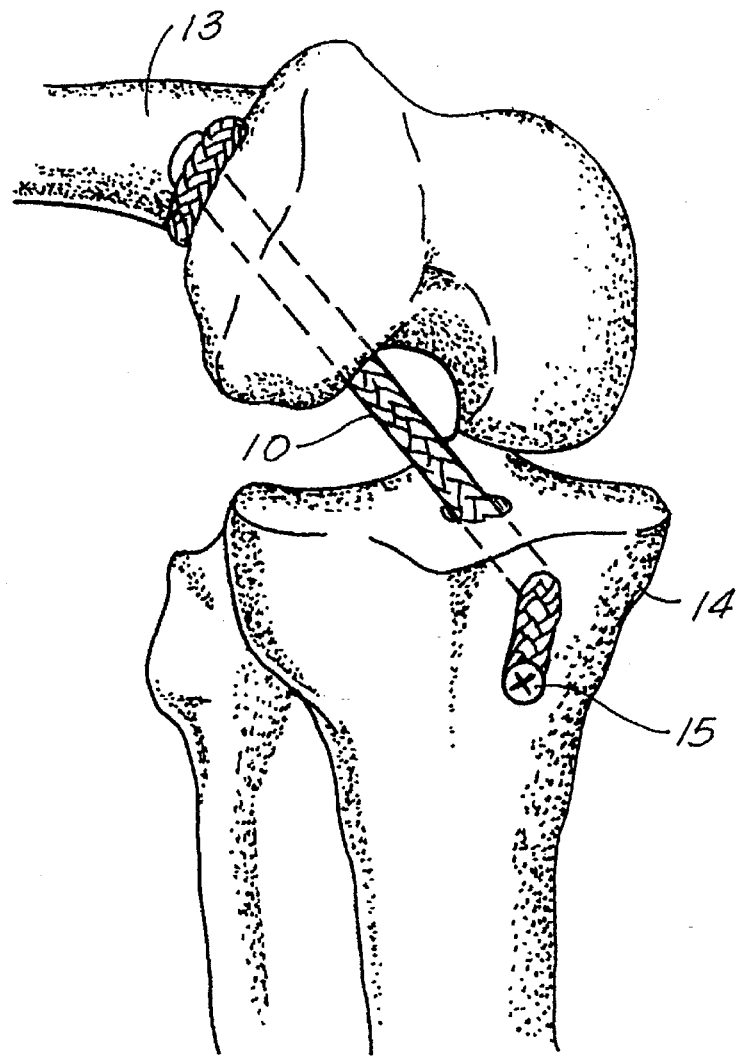
FIG. 3 is a pictorial view of the load bearing cable of the present invention as applied to the repair of a torn ligament.
Figure 4:
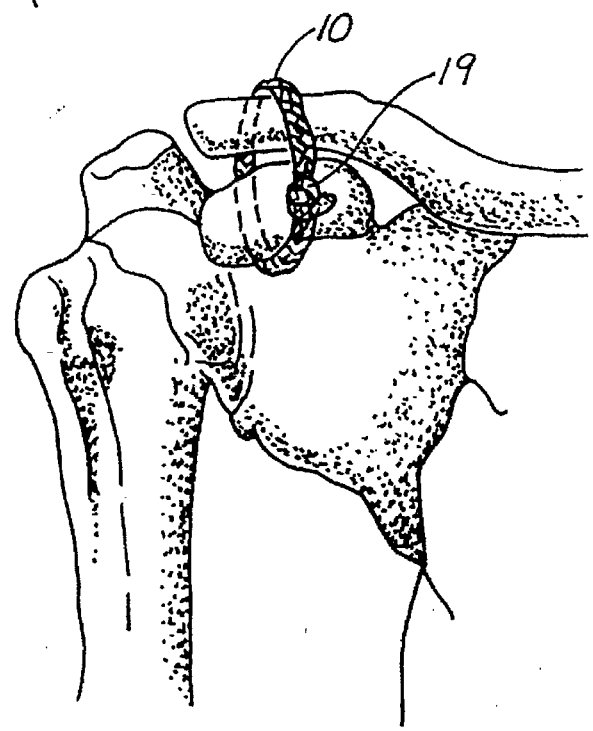
FIG. 4 is a pictorial view of the load bearing cable of the present invention as applied to the repair of a clavicular ligament.

As shown in FIG. 2, the patella 16 is a small bone which covers the anterior compartment of the knee joint. Superiorly it is attached to the tendon of the quadriceps muscle group and interiorly, it is attached to the patellar ligament 17, which inserts into the anterior surface 18 of the tibia 14. The patella 16 functions to enhance the lever arm of the muscles which extend the leg. As such, the patella 16 is loaded in tension, having an approximate superior-inferior direction.

When the patella 16 is fractured in a transverse direction, perpendicular to the line of force, apposition of the patella fragments and compressive force is required to keep the fragments in close approximation for healing. Generally, surgical wire has been used to bend tightly around the patella 16, twisting two ends of a wire together to provide compressive force. This application method often results in wire breakage. In addition, post implantation wire fatigue caused by high tensile stresses from the quadriceps muscle group during extension of the leg often causes surgical wire to fail. Failure of the wire to apply sufficient compressive force or failure or intimate apposition of patella fragments due to wire breakage results in a reduced or failed healing of the bone. Sharp wire points caused by wire breakage in situ can result in significant damage to surrounding tissues and may even penetrate the knee joint capsule.

The load bearing cable 10 of the present invention is substituted for surgical wire in repair of patella 16 fractures. The cable material is wrapped tightly around the patella 16 with two ends 19 tied together tightly to provide compressive force. The cable 10 has sufficient tensile strength to maintain the patella fragments in close approximation and promote active healing, and is sufficiently inelastic to prevent separation of the patella 16 fragments under tensile loading. The load bearing cable is less susceptible to fatigue failure than surgical wire. In the event the cable does fail, no threat of damage to surrounding tissues is posed.

When the cable is formed of a bioresorbable polymeric fiber, stress will gradually be transferred to the patella in a controlled manner, as the cable is resorbed, enhancing healing per Wolff's law, bone remodels in response to applied stress.

EXAMPLE 6

Fusion of Spinal Vertebrae

Current procedures for repair or fusion of the spinal column restrict motion of vertebral bodies by fixing posterior elements of the vertebrae, transverse processes and pedicles, together, inserting a bone graft along the posterior surface of the spinal column, and then fixing the graft into position. Satisfactory fusion requires that the vertebrae remain sufficiently immobilized to permit healing of the bone graft to the vertebrae.

In general, surgical wire has been used in this procedure. Problems with the use of surgical wire in spinal fusions are similar to those encountered with the patella fusion described for Example 5, including wire breakage during insertion or tensioning, failure to maintain adequate compressive force, and fatigue of wire over time. In addition the proximity of the spinal cord to the fusion site makes the consequences of wire breakage life threatening.

These problems are circumvented by use of the load bearing cable of the present invention as described in Example 5. As shown, for example in FIG. 1, the surgical cable 10 of the present invention is substituted for surgical wire in the fixation of the posterior elements 20 of the vertebrae and fixation of the graft into position. The surgical cable of the present invention provides sufficient compression and tensile strength to maintain the vertebral processes and/or graft in close approximation for fusion and healing.

When a bioresorbable fiber cable is used, stresses transferred to the bone graft in a controlled manner as the cable is resorbed, resulting in enhanced healing and greater success rate.

Having described the invention above, various modifications of the techniques, procedures, material and equipment will be apparent to those in the art. It is intended that all such variations within the scope and spirit of the appended claims be embraced thereby.

In FIGS. 7 and following present invention provides a cable attachment apparatus 25 for the surgical repair or fusion of anatomical structures. FIG. 7 illustrates a cable attachment apparatus 25 being used to stabilize adjacent human vertebrae V of a human spinal column S. The cable attachment apparatus 25 (FIG. 8) is constructed from a length of flexible cable 26 formed of braided polymeric material. The cable 26 has a central portion 27, first and second end portions 28, 30 and first and second cable ends 29, 31.

A first adjustable loop 37 is formed in a portion of the cable 26 by tying a first non-self-loosening know 32 which is capable of being adjusted by pulling the cable end portion 29 (FIG. 9). The first adjustable loop 37 is formed with the end portion 30 of the cable 26 by tying a first non-self-loosening knot 32 which is capable of being adjusted by pulling the end 29 of cable end portion 28 in order to reduce the circumference of the first loop 37.

In FIG. 9, the first loop 37 can be formed using knot 32 which is similar to a clinch knot, for example. Clinch knots per se are known, being used most commonly in the prior art by fishermen to secure monofilament line to a fish hook eye. Published literature describes the procedure for tying a clinch knot. Variations of a clinch knot are in published literature of fishing line manufacturers, e.g., Berkley Outdoor Technology Group of Spirit Lake, Iowa (Berkley describes a knot in its literature as the "Trilene Knot"). Knot 32 can be formed by making several turns 34 (e.g., five (5) turns) of the end 30 of the line 26 around the central 27 part of the line 26. In FIG. 9, the tag end is free end 30 and the standing part is end portion 29. The five (5) turns are shown as twists 34 in FIG. 9. The end portion 30 is inserted through the loop 37 (see arrows 35, 36) forming a temporary loop 37. The end portion 30 is then inserted through the just formed temporary loop (see arrows 39, 40) and tightened by pulling the portion 30 to close temporary loop 38. The completed knot 37 is shown in FIG. 10.

Figure 10:
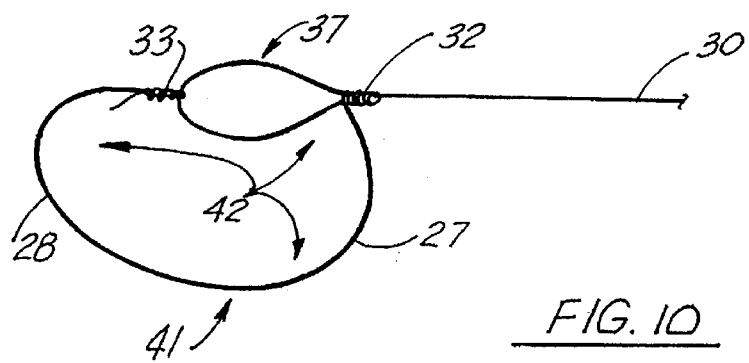
FIG. 10 is a top plan view of the present invention illustrating the first and second non-self-loosening knots.

A second adjustable loop 41 is formed in portion 27 of the cable for threading around or through an anatomical structure or other object designated schematically as anatomical structure 45 (FIG. 10). The loop 44 is tied to the loop 37 with a second non-self-loosening knot 33. The knot 33 is formed after the loop 41 has been secured around or through the structure 42 to be tied.

The braided polymeric cable 26 is made of fibers formed of a high strength, biocompatible, organic polymer, preferably polyolefins such as ultra high molecular weight polyethylene. In a preferred embodiment the cable 26 is formed of Spectra-1000 and the cable attachment apparatus 25 can be formed of braided polymeric cables of a variety of diameters.

Figure 17:
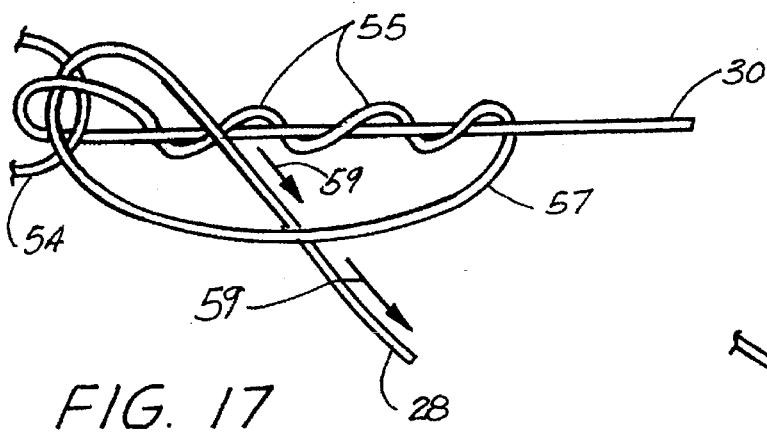

The invention is also directed to a method of forming the cable attachment apparatus 25. The cable attachment apparatus 25 is constructed from the length of flexible cable 26 (FIG. 8) by forming a first adjustable loop 37 by wrapping the cable end 30 around a portion of the cable 28, between the first and second cable ends 29, 31, a plurality of turns 34 as illustrated in FIG. 9. The cable end 30 is passed through the loop 37 to create a second loop parallel to the plurality of twists 34 (FIG. 9). Cable end 30 is then passed back through the temporary loop 38 and tightened to create the non-self-loosening knot 32 as shown in FIGS. 10 and 17.

Figure 19:
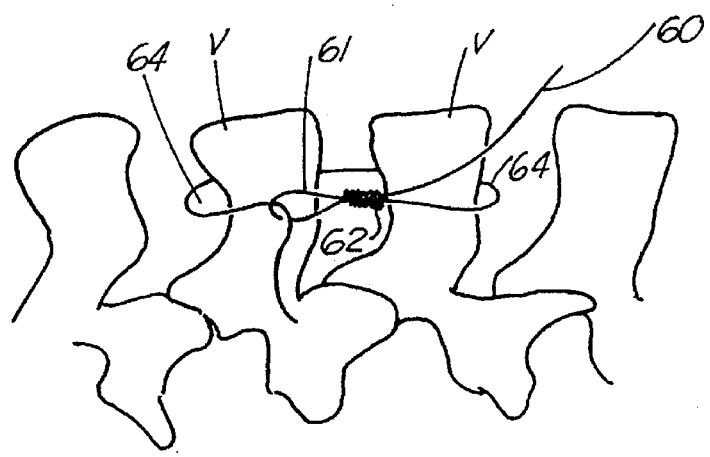

The cable end 29 is then threaded around or through the object to be tied, forming a second adjustable loop 41. After the cable end 29 is threaded around or through the object, the end 29 is tightened to reduce the slack in the loop 37 and tied to the loop 37 with a non-self-loosening knot 33. The non-self-loosening knot 33 is formed by passing the cable end 28 through the loop 37 at least one turn, on the side of the loop 36 opposite the non-self-loosening knot 32, and forming a plurality of half hitches 41 (FIG. 11) between the cable end and a portion of the cable (FIGS. 10 and 19).

Figure 11:
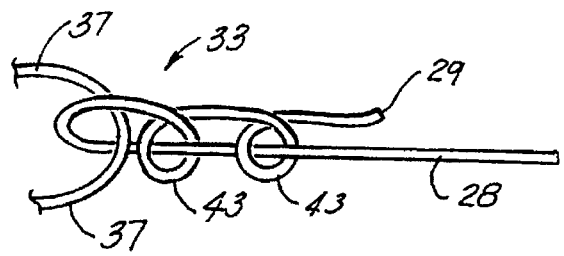
FIG. 11 is a top plan view of the second non-self-loosening knot of the present invention.

As illustrated in FIG. 11, the half hitches 43 are formed bypassing the cable end 29 through the loop 37, looping cable end 29 under and around the loop portion 37, then looping the end 29 again under and around the loop portion 37 forming a second half hitch, and pulling the cable end 29 taut to create the non-self-loosening knot 33.

The cable end portion 30 is then tightened to reduce the size of the loop 37 which causes the cable attachment apparatus 25 to be tensioned and securely held around or through the object being tied.

Figure 12:
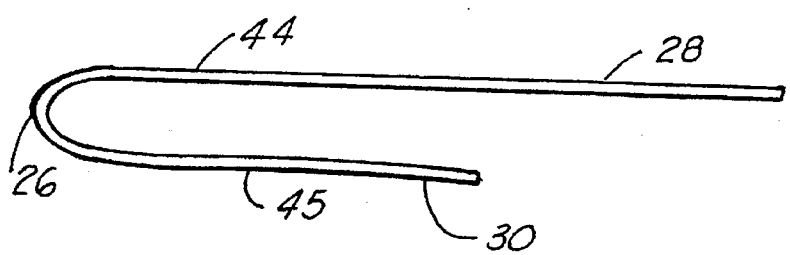
FIGS. 12–14 are top plan views of the formation of an alternate first non-self-loosening knot of the present invention.
Figure 13:
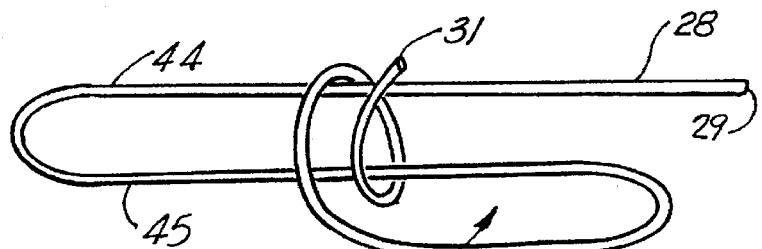
Figure 14:
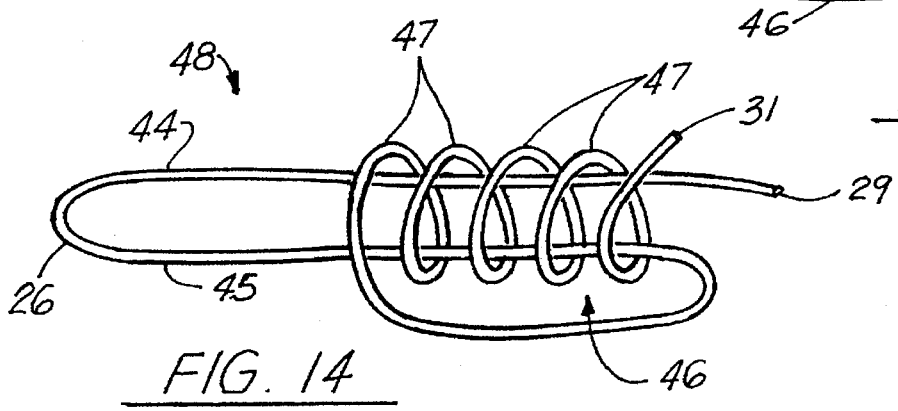
Figure 15:
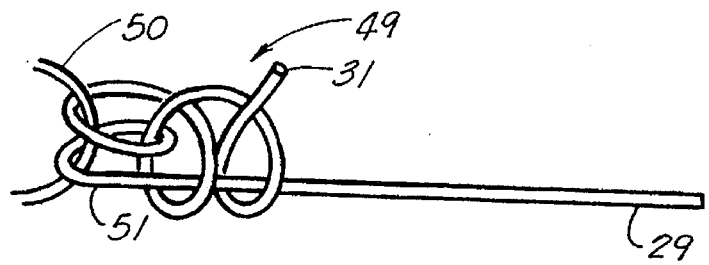
FIG. 15 is a top view of an alternate second non-self-loosening knot of the present invention.

As illustrated in FIGS. 12–14, an alternate method of forming the adjustable loop is by positioning the two portions 44, 45 of the cable 12 between the first and second cable ends 28, 30 parallel to each other (FIG. 12). A temporary loop 46 is formed (FIG. 13). The cable end 31 is then wrapped around the two parallel portions 44, 45 and through the temporary loop 46 to form a plurality of turns 47 and tightened to create the non-self-loosening knot 48 (FIG. 14). Alternately, a non-self-loosening knot 49 can be formed by passing the cable end through loop 50 at least three times, forming loops, and then tying a fisherman's bend knot between the cable end and a portion of the loop on the side of the loop opposite the knot. The fisherman's bend knot is illustrated in FIG. 6 and is formed bypassing the cable end 31 around the loop 50 a plurality of times forming loops 51, 52. The cable end 31 is brought down over the end portion and up through the loops 51, 52 and then a second half hitch as described above is formed.

Figure 16:
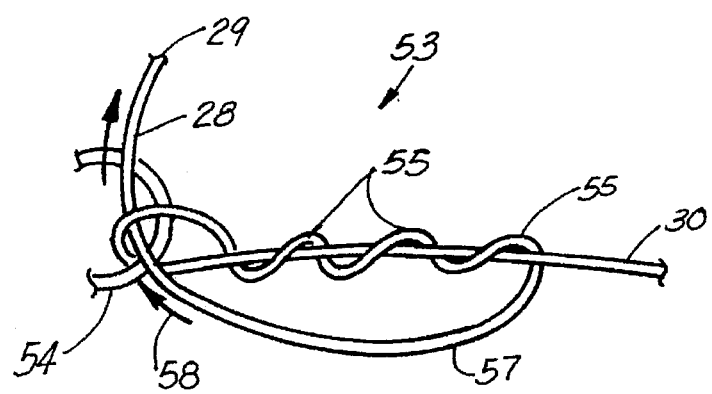
FIGS. 16–17 are top plan views of the formation of a further alternate second non-self-loosening knot of the present invention.
Figure 18:
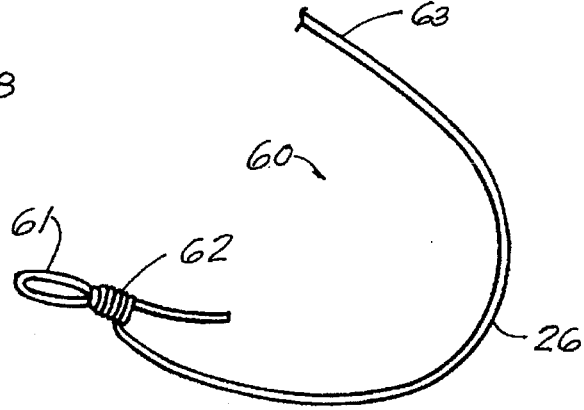
FIGS. 18–20 are top and side plan views of steps for utilizing an embodiment of the present invention to stabilize adjacent vertebrae.

Another method of forming the non-self-loosening knot is shown in FIGS. 16–18. A clinch knot 53 is formed by first passing the cable end 29 through the loop 54 and then wrapping end 29 around a portion of loop end 30 a plurality of turns 55. The cable end 29 is next threaded up through the loops 56 (see arrows 58) (FIG. 16) forming a loop 57 and then back down through (see arrows 59) loop 57 and tightened (FIG. 17).

In an alternate embodiment of the cable attachment apparatus designated as 60, the loop 61 and knot 62 are preformed. Cable attachment device 60 is shown in FIG. 18 having a preformed adjustable loop 61 and a partially tightened non-self-loosening knot 62. A blunt tipped needle 63 is attached to the cable end 26 so as to allow easier threading of the cable end 14 around or through the object to be tied. The needle can be curved or straight and after the cable attachment device 60 is tensioned and secured in place the needle 63 is removed from the cable end.

Figure 20:
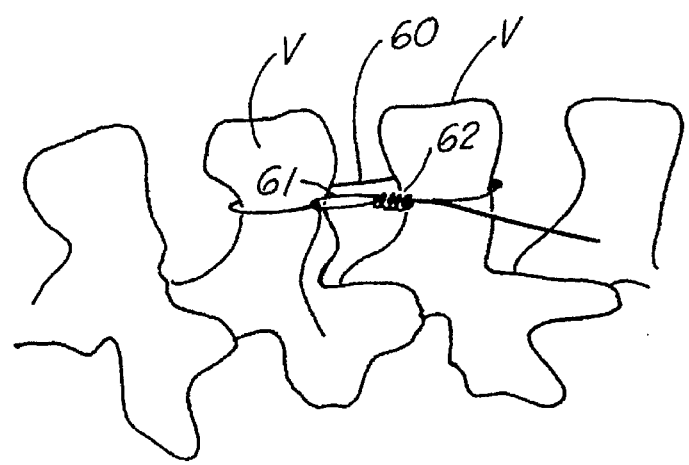

An example of the cable attachment device 60 being used to stabilize adjacent vertebrae is illustrated in FIGS. 19-20. The preformed loop 61 of the device 60 is placed along side one of the vertebrae V to be stabilized. The cable end with the needle 63 is wrapped around the adjacent vertebrae V forming the loop 64. The needle 63 is then threaded through the loop 61 and the cable end 19 is tightened in order to remove the slack in loop 64 (FIG. 19). The non-self-loosening knot 62 is tied and the cable end is tightened in order to tension and secure the cable attachment device 60 around the adjacent vertebrae.

Figure 21:
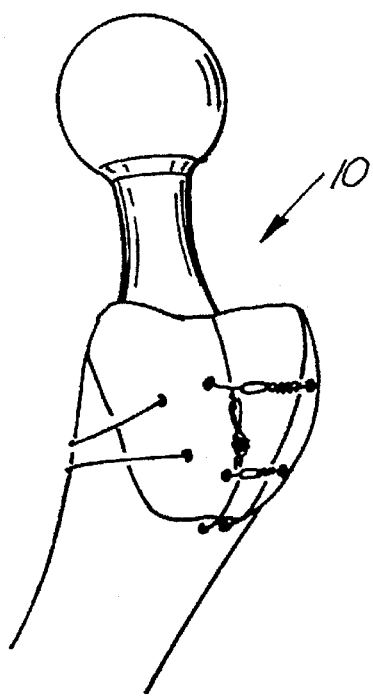
FIGS. 21–22 illustrate alternate embodiments of the present invention as used to connect specific bones together.
Figure 22:
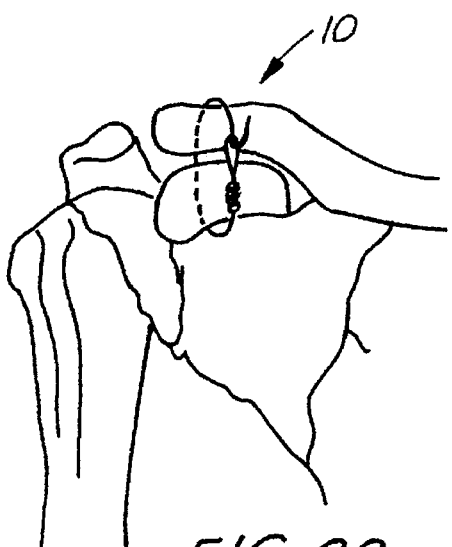

The cable attachment apparatus 10 can be used for the surgical repair or fusion of anatomical structures and for use as a securing device in non-medical applications. For example, the cable attachment apparatus can be used for the repair of fractures or fusions of any small bones, it can be used to hold together fragments of the patella or in the repair of tendons and ligaments such as those found in the clavicle. The cable attachment apparatus can also be used wherever wire, heavy sutures or staples are used in a medical procedure. For example, in trochanteric reattachment procedures the cable apparatus can be used in place of monofilament wire (FIG. 21).

Figure 23:
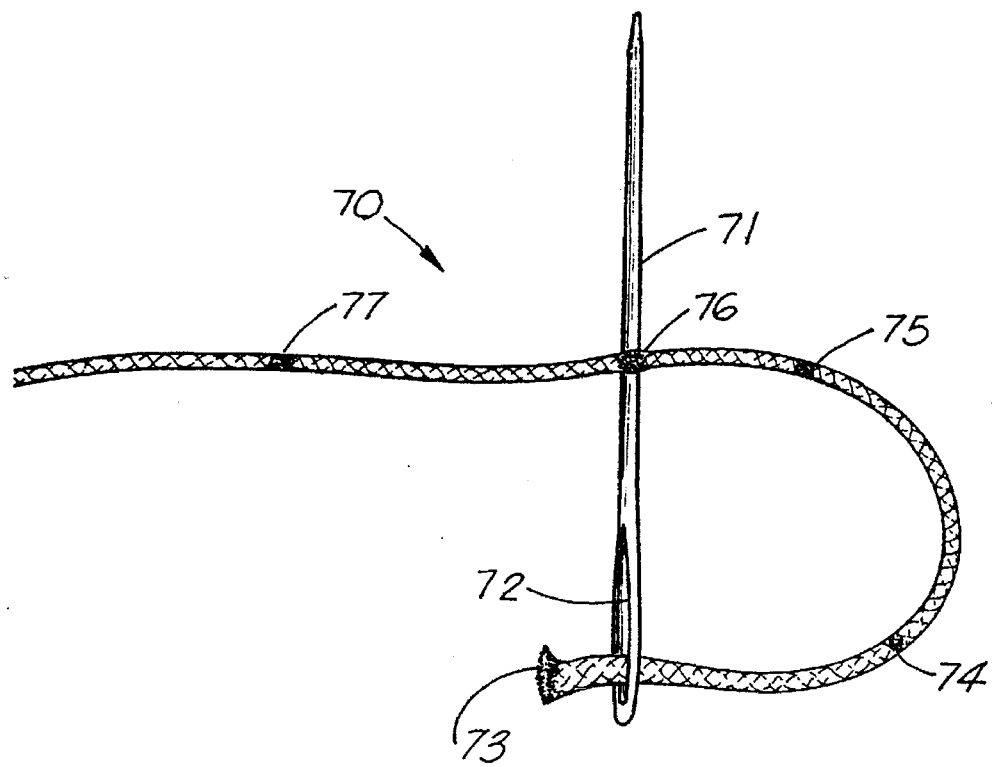
FIGS. 23–29 are schematic sequential views that illustrate a preferred method for creating an eye splice on the end of the cable portion of the method of the present invention.

FIGS. 23-29 illustrate a method for creating an eye splice on an end of a length of cable 70 opposite a surgical needle. In FIG. 23, a desired length of cable 70 is shown having sewing needle 71 attached at it eye 72 to end 73 of cable 70. Cable 70 can be provided with marks 74-77 at intervals of for example 1 inch, 2 inches, 2.5 inches, 3.5 inches from the end 73 of cable 70.

Figure 24:
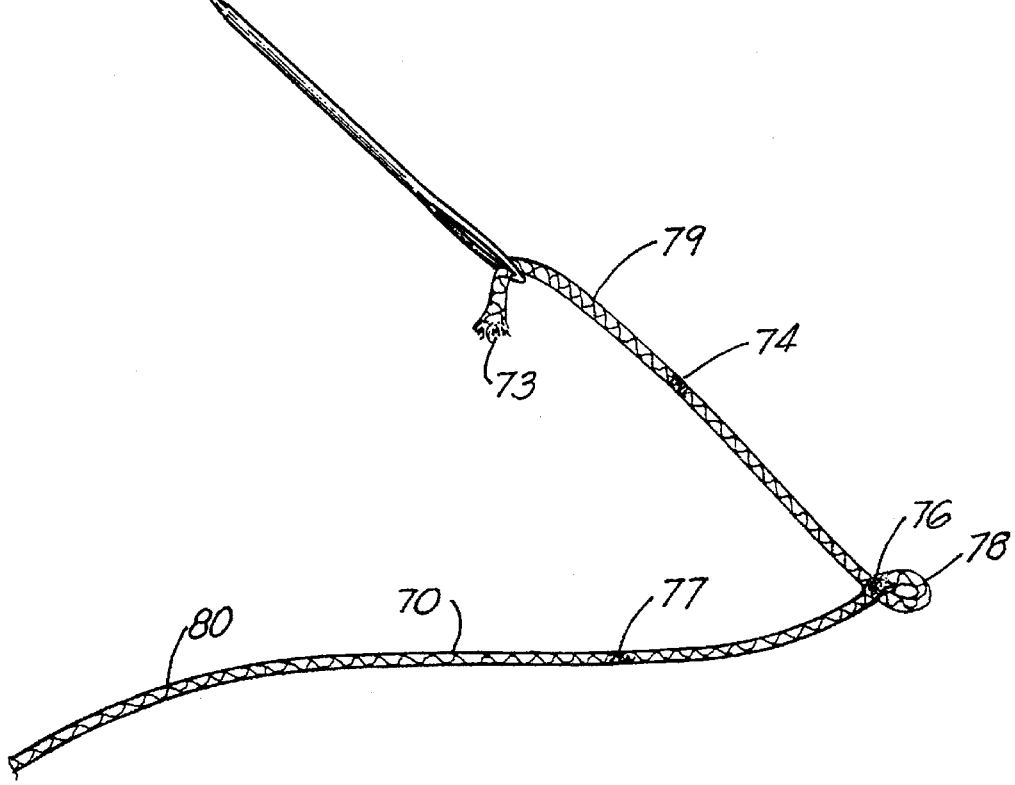
Figure 25:
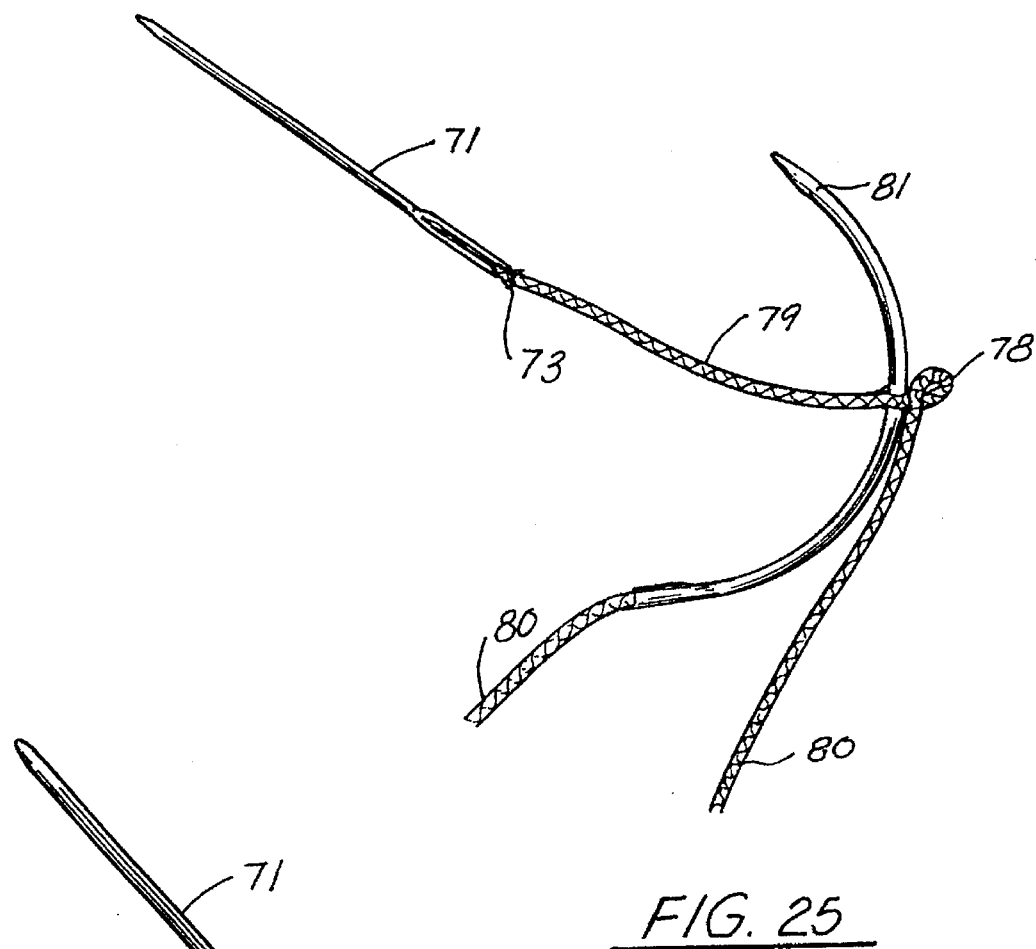
Figure 26:
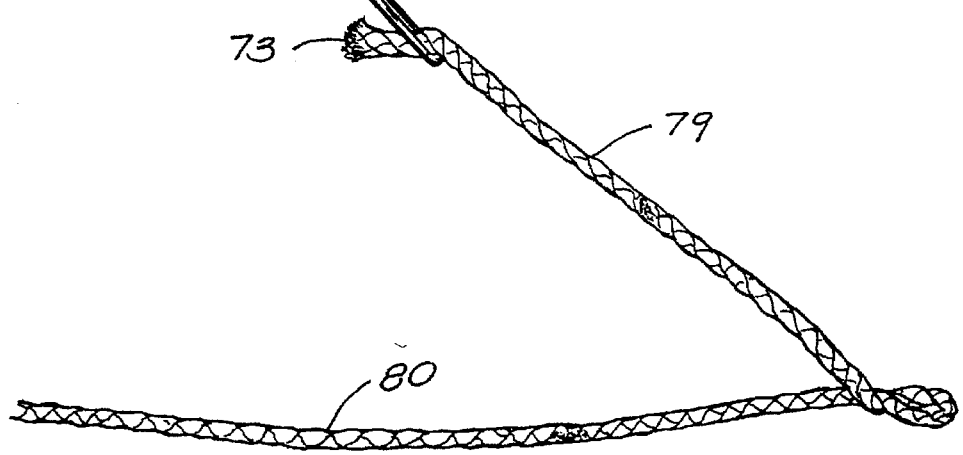
Figure 27:
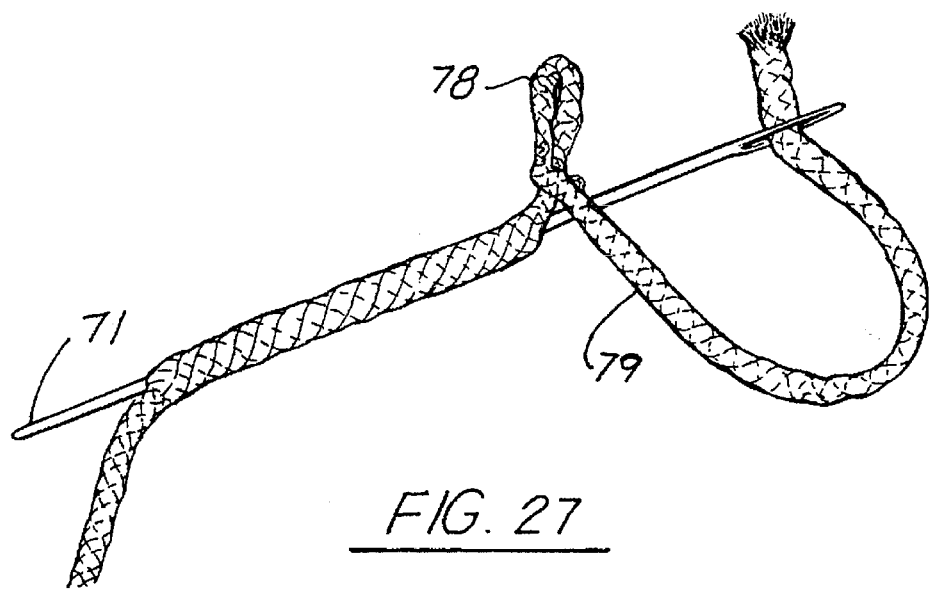
Figure 28:
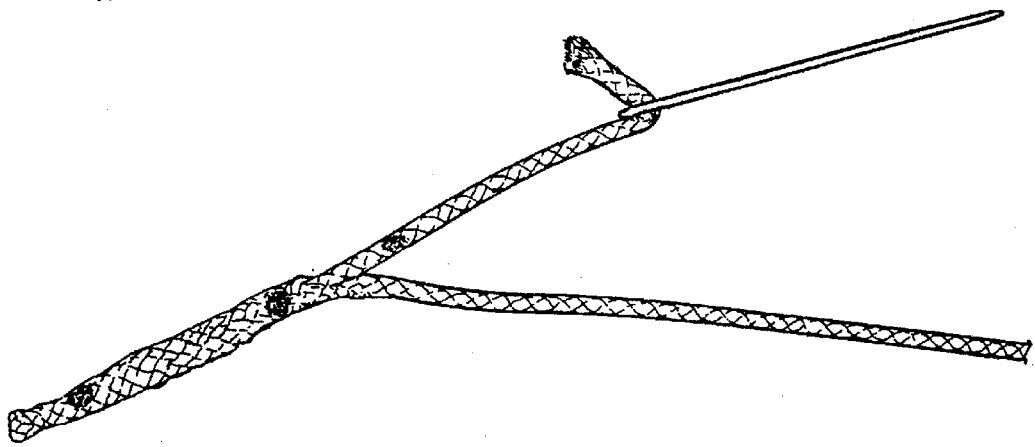
Figure 29:
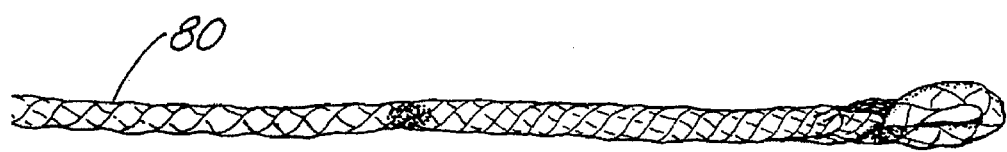

The user passes the end 73 of the cable 70 and sewing needle 71 through the middle of the cable 70 at the third mark 76 (see FIG. 23). The end 73 of cable 70 is then pulled through until the second mark 75 passes to the cable. This produces a small eye 78 as shown in FIG. 24. The cable now has a short section (tail) 79 and a long section (standing line) 80. The long section 80 has a surgical needle 81 attached thereto (see FIG. 25). The user then holds the eye 78 just constructed and threaded the long 80 section of cable 70 (with the surgical needle 81 attached) through the short end 79 at a position adjacent the eye 78 as shown in FIG. 25. In FIG. 26, the user then pulls the long 80 end until no more slack exists. The short end 79 of cable 70 is then buried by placing the sewing needle 71 through the center of the cable adjacent the eye 78. The sewing needle 71 should exit the cable of few picks past the last mark 77. Scissors can be used to cut off any excess at the end 73. The standing line 80 is then pulled to insure that the end of the tail 79 is buried in the middle of the cable as shown in FIG. 29.

FIGS. 30-36 illustrate the method of the present invention using the eye splice, cable and needle constructed in FIGS. 23-29.

In FIGS. 30-32, a splicing technique is shown. The surgical needle 78 is passed through the eye 78 and then through the center of the cable 70 at position 82 in FIG. 30. This step is repeated three more times for a total of 4 moving away from the loop end 78 as shown in FIG. 31. In FIG. 31, the needle passes through the cable at positions 82-85, forming loops 86-89. A tensioner can be used to tighten the knot, but is not necessary. The knot can be tightened without such a tensioner. If a tensioner is to be used, the needle is placed through a hole in the tip of a tensioner shown in FIG. 32 then through the latch in the center of the tensioner. The cable is then tightened with the tensioner and the cable 70 and needle removed from the tensioner. As a last optional step (see FIG. 31A), the needle 81 can be used to pass the needle end of the cable 70 through the tightened knot.

Figure 33:
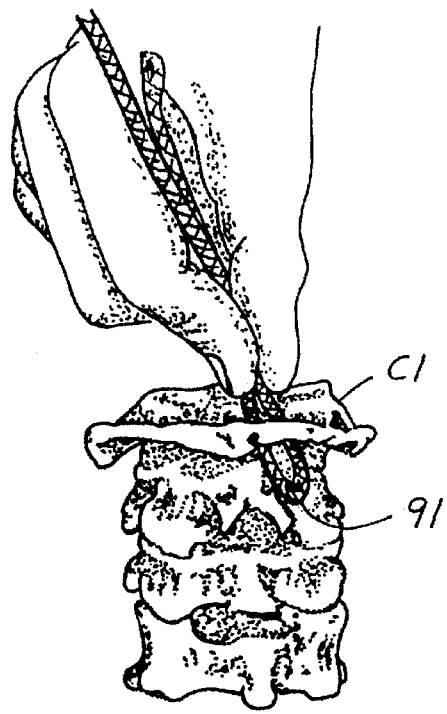
FIGS. 33–36 are schematic sequential views illustrating the method of the present invention.

FIGS. 33-36 illustrate surgical technique using the cable, needle and splicing that is shown and described in FIGS. 23-32. In FIG. 33, the cable 70 is doubled at its central portion and passed underneath the arch of vertebrae C1, designated as C1 in FIG. 33. A loop 90 is formed when the cable is doubled, in FIG. 3 the loop can be seen after passing underneath the arch of C1.

Figure 34:
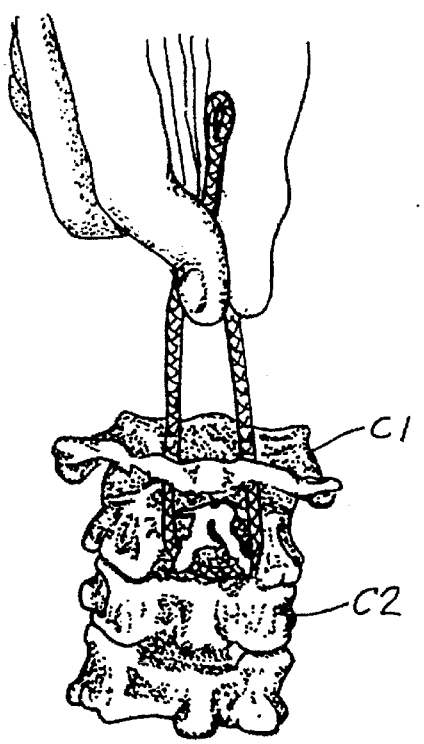
Figure 35:
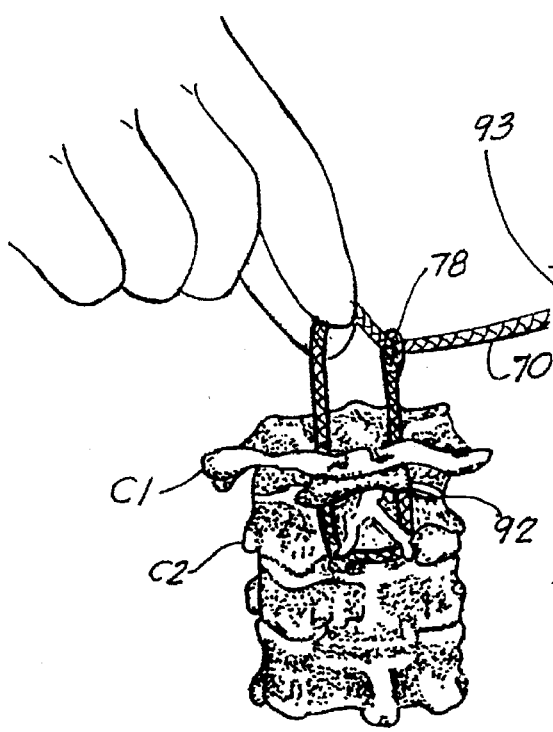
Figure 36:
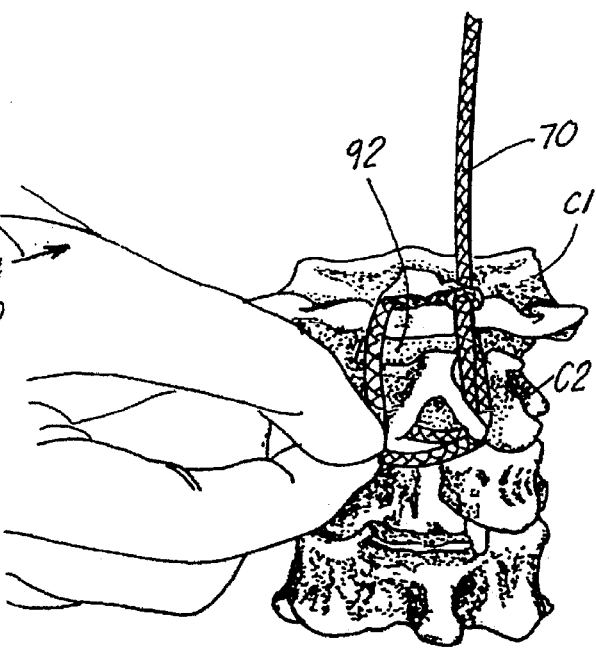

In FIG. 34, the loop 91 has been wrapped around the spinous process of C2. At this point, the surgeon places bone graphed material designated as 91 in FIG. 35. After the bone graph material 91 has been placed between C1 and C2, the surgeon then passes the surgical needle 81 through the eye 78 as shown by arrow 93 in FIG. 35. In FIG. 36, the surgeon then wraps the cable 70 over the bone graph 92 and underneath the spinous process of C2. The cable is then secured using the splicing technique described with reference to FIGS. 30-32.

FIGS. 37-39 illustrate the surgical technique using the cable needle and splicing that is shown in and described in FIGS. 23-32. In FIG. 37, the needle 81 and cable 70 are passed through a hole that has been drilled through the spinous process. In FIG. 38 a piece of bone graft material B has been inserted between the two adjacent spinous processes. After the bone graft material is placed between the spinous processes, the cable 70 is wrapped around the adjacent spinous process and the surgical needle 81 is passed through the eye 78. The cable 70 is then tightened around the spinous processes (FIG. 39) and secured using the splicing technique described with reference to FIGS. 30-32 and 31A.

This splicing fixation technique of FIGS. 23-39 may be used in the same applications as the techniques shown in FIGS. 7-22. In particular it is ideally suited for use in spinal fusions, olecranon fracture repair, patellar fracture repair, trochanteric reattachment, tendon and ligament reattachment, acromioclavicular (AC) Joint repair, rotator cuff repairs, ceriage and other general orthopaedic repair procedures.

It should be understood that there can be improvements and modifications made to the embodiments of the invention described in detail above without departing from the spirit or scope of the invention, as set forth in the accompanying claims.

The following table lists the parts numbers and parts description as used herein and in the drawings attached hereto.

| PARTS LIST | |
| --- | --- |
| Part Number | Description |
| 10 | load bearing cable |
| 11 | yarns |

-continued

PARTS LIST

| Part Number | Description |
|---|---|
| 12 | stands |
| 12a | axis |
| 13 | femur |
| 14 | tibia |
| 15 | screws |
| 16 | patella |
| 17 | patella ligament |
| 18 | anterior surface |
| 19 | ends |
| 20 | posterior elements |
| 21 | needle |
| V | vertebrae |
| S | spinal column |
| 25 | cable attachment apparatus |
| 26 | flexible cable |
| 27 | central portion |
| 28 | first end portion |
| 29 | first end |
| 30 | second end portion |
| 31 | second end |
| 32 | non-self-loosening knot |
| 33 | non-self-loosening knot |
| 34 | twists |
| 35 | arrow |
| 36 | arrow |
| 37 | first adjustable loop |
| 38 | temporary loop |
| 39 | arrow |
| 40 | arrow |
| 41 | second adjustable loop |
| 42 | anatomical structure |
| 43 | half hitch |
| 44 | cable section |
| 45 | cable section |
| 46 | temporary loop |
| 47 | turns |
| 48 | knot |
| 49 | knot |
| 50 | loop |
| 51 | loop |
| 52 | loop |
| 53 | clinch knot |
| 54 | loop |
| 55 | turns |
| 56 | loop |
| 57 | loop |
| 58 | arrow |
| 59 | arrow |
| 60 | cable attachment |
| 61 | loop |
| 62 | knot |
| 63 | needle |
| 64 | loop |
| 70 | cable |
| 71 | needle |
| 72 | eye |
| 73 | end |
| 74 | mark |
| 75 | mark |
| 76 | mark |
| 77 | mark |
| 78 | eye |
| 79 | tail section |
| 80 | standing line |
| 81 | needle |
| 82 | position |
| 83 | position |
| 84 | position |
| 85 | position |
| 86 | loop |
| 87 | loop |
| 88 | loop |
| 89 | loop |
| 90 | tensioner |
| 91 | loop |
| 92 | bone graft |

-continued

PARTS LIST

| Part Number | Description |
|---|---|
| 93 | arrow |
| C1 | vertebra |
| C2 | vertebra |

What is claimed is:

1. A surgical cable apparatus for surgically securing and fusing vertebral bone segments together, wherein each of the vertebral bone segments having an irregular outer surface, comprising:

a) a flexible surgical cable member having first and second free end portions;

b) a needle attached to the first of one of said free end portions, the flexible cable being formed of a plurality of polymeric fibers;

c) the flexible cable being of a diameter of between one and three (1–3) millimeters along the entire length thereof including said first and second free end portions;

d) said cable having sufficient inherent flexibility for enabling the cable to be wrapped around the irregular outer surface of the vertebral bone segments and in close conformity with the irregular outer surfaces of the vertebral segments;

e) a splice connection for joining the cable end portions together after the cable has been wrapped around the bone segments to be fused, said splice connection including a woven interconnection of the cable end portions wherein the first end portions weaves between individual fiber strands of the second end portion; and f) wherein the flexible cable can transfer sufficient compressive force to the bone segments to hold them in position while the bone heals and fuses together over time.

2. The surgical cable apparatus of claim 1 wherein the cable is an olefin.

3. The surgical cable apparatus of claim 2 wherein the cable is comprised of a plurality of fibers of an ultra high molecular weight olefin.

4. The surgical cable apparatus of claim 1 wherein the cable is formed of a plurality of groups of fibers that are woven together.

5. The surgical cable apparatus of claim 1 wherein the splice connection includes an interwoven interface that includes two interwoven sections of the flexible cable.

6. The surgical cable apparatus of claim 5 wherein the needle is spaced away from the splice correction upon completion of the splice connection.

7. The surgical cable apparatus of claim 1 wherein the cable is flexible enough to conform to bony prominences of the vertebral bone segments.

8. The surgical cable apparatus of claim 1 further comprising a second flexible surgical cable.

9. The surgical cable apparatus of claim 8 wherein the needle includes a leader and a branch that carries the pair of cables.

10. The surgical cable of claim 1 further comprising a second cable and a second needle attached to an end portion of the second cable and wherein the two needle portions are removably connected together so that a surgeon can pass the pair of needles and a corresponding pair of cables through selected tissue or through spaces in between selected tissue.

11. The cable attachment apparatus of claim 1 wherein the polymeric fibers formed of a high strength, biocompatible, and organic polymer.

12. A surgical cable apparatus for surgically securing and fusing bone segments together, wherein each of the bone segments having an irregular outer surface, comprising:
   a) a flexible surgical cable member having first and second free end portions;
   b) the flexible cable being formed of a plurality of polymeric fibers;
   c) the flexible cable being of a diameter of between one and three (1-3) millimeters along the entire length thereof including said first and second free end portions;
   d) said cable having sufficient inherent flexibility for enabling the cable to be wrapped around the irregular outer surface of the bone segments and in close conformity with the irregular outer surfaces of the segments;
   e) a connection for joining the cable end portions together after the cable has been wrapped around the bone segments to be fused; and
   f) wherein the flexible cable can transfer sufficient compressive force to the bone segments to hold them in position while the bone heals and fuses together over time.

13. The cable attachment device of claim 12 wherein the polymeric fibers formed of a high strength, biocompatible, organic polymer.

14. The cable attachment of claim 12 wherein the polymer is ultra-high molecular weight polyethylene.

15. The cable attachment device of claim 12 wherein one of the cable ends includes a needle.

16. A surgical cable apparatus for surgically securing bone segments together while they fuse, wherein at least one of the bone segments having an irregular outer surface, comprising:
   a) a flexible surgical cable member having first and second free end portions;
   b) the flexible cable being formed of a plurality of polymeric fibers;
   c) the flexible cable being of a diameter of between one and three (1-3) millimeters along the entire length thereof including said first and second free end portions;
   d) the cable being flexible enough so that a user can form multiple knots at selected positions along the length thereof;
   e) said cable having sufficient inherent flexibility for enabling the cable to be wrapped around the irregular outer surface of the bone segments and in close conformity with the irregular outer surfaces of the segments;
   f) a connection for joining the cable end portions together after the cable has been wrapped around the bone segments to be fused; and
   g) wherein the flexible cable can transfer sufficient compressive force to the bone segments to hold them in position while the bone heals and fuses together over time.

17. The surgical cable apparatus of claim 16 wherein the cable is an olefin.

18. The surgical cable apparatus of claim 17 wherein the cable is comprised of a plurality of fibers of an ultra high molecular weight olefin.

19. The surgical cable apparatus of claim 16 wherein the cable is formed of a plurality of groups of fibers that are woven together.

20. The surgical cable apparatus of claim 16 wherein the cable is flexible enough to conform to bony prominences of the vertebral bone segments.

21. The cable attachment apparatus of claim 16 wherein the polymeric fibers formed of a high strength, biocompatible, and organic polymer.

22. The cable attachment of claim 16 wherein the polymer is ultra-high molecular weight polyethylene.

* * * * *